(12) United States Patent
Kilawee et al.

(10) Patent No.: US 7,195,744 B2
(45) Date of Patent: Mar. 27, 2007

(54) DEVICE FOR HOLDING A CONTAINER FOR A COMPOSITION THAT PRODUCES AN ANTIMICROBIALLY ACTIVE GAS

(75) Inventors: Patrick H Kilawee, Hugo, MN (US); Daniel N Tallman, Roseville, MN (US); Leonard J Kadlec, Woodbury, MN (US)

(73) Assignee: Ecolab, Inc., St. Paul, MN (US)

( * ) Notice: Subject to any disclaimer, the term of this patent is extended or adjusted under 35 U.S.C. 154(b) by 931 days.

(21) Appl. No.: 09/941,505

(22) Filed: Aug. 28, 2001

(65) Prior Publication Data

US 2003/0205051 A1 Nov. 6, 2003

(51) Int. Cl.
*A61L 2/20* (2006.01)

(52) U.S. Cl. .................. 422/305; 422/300; 422/37; 62/78; 62/303

(58) Field of Classification Search ............... 422/300, 422/305, 37; 62/78, 303
See application file for complete search history.

(56) References Cited

U.S. PATENT DOCUMENTS

| | | | | |
|---|---|---|---|---|
| 4,059,048 A | * | 11/1977 | Dickson | 99/482 |
| 4,123,130 A | * | 10/1978 | Locke | 312/285 |
| 4,258,056 A | | 3/1981 | Lentsch | 424/303 |
| 4,284,653 A | | 8/1981 | Shigeoka et al. | 426/312 |
| 4,297,224 A | | 10/1981 | Macchiarolo et al. | 210/755 |
| 4,324,635 A | | 4/1982 | Sweeney | 204/266 |
| 4,325,934 A | | 4/1982 | Swindells et al. | 423/478 |
| 4,330,531 A | | 5/1982 | Alliger | 424/149 |
| 4,370,305 A | | 1/1983 | Affonso | 422/292 |
| 4,376,787 A | | 3/1983 | Lentsch et al. | 424/315 |
| 4,437,575 A | * | 3/1984 | Hahn | 220/87.1 |
| 4,460,373 A | | 7/1984 | Beavan | 8/103 |
| 4,542,008 A | | 9/1985 | Capuano et al. | 423/477 |
| 4,547,381 A | | 10/1985 | Mason et al. | 426/316 |
| 4,585,482 A | | 4/1986 | Tice et al. | 106/15.05 |
| 4,683,039 A | * | 7/1987 | Twardowski et al. | 205/500 |
| 4,689,169 A | | 8/1987 | Mason et al. | 252/186.24 |
| 4,832,972 A | | 5/1989 | Toledo-Flores et al. | 426/327 |
| 5,091,107 A | | 2/1992 | Hutchings | 252/187.21 |
| 5,165,181 A | * | 11/1992 | Acosta et al. | 34/90 |
| 5,193,357 A | | 3/1993 | Kohl et al. | 62/347 |
| 5,225,172 A | * | 7/1993 | Meyler et al. | 422/300 |
| 5,229,072 A | | 7/1993 | Tarancon | 422/37 |
| 5,289,691 A | | 3/1994 | Schlosser et al. | 62/78 |
| 5,360,609 A | | 11/1994 | Wellinghoff | 514/772.3 |
| 5,382,520 A | | 1/1995 | Jenson et al. | 436/55 |
| 5,408,834 A | | 4/1995 | Schlosser et al. | 62/78 |
| 5,442,938 A | * | 8/1995 | Kislyuk | 68/5 C |
| 5,476,579 A | | 12/1995 | Choi et al. | 204/95 |
| 5,586,439 A | | 12/1996 | Schlosser et al. | 62/78 |
| 5,631,300 A | | 5/1997 | Wellinghoff | 514/722.3 |
| 5,639,295 A | | 6/1997 | Wellinghoff et al. | 106/15.05 |

(Continued)

FOREIGN PATENT DOCUMENTS

DE 2155815 A * 5/1973

(Continued)

*Primary Examiner*—E. Leigh McKane
(74) *Attorney, Agent, or Firm*—Kinney & Lange, P.A.

(57) ABSTRACT

A device and method for cleaning and deodorizing a unit having an enclosed space not otherwise easily accessible for cleaning and deodorizing.

12 Claims, 4 Drawing Sheets

U.S. PATENT DOCUMENTS

| | | | |
|---|---|---|---|
| 5,639,559 A | 6/1997 | Mason et al. | 423/472 |
| 5,650,446 A | 7/1997 | Wellinghoff et al. | 514/772.3 |
| 5,695,814 A | 12/1997 | Wellinghoff et al. | 427/213 |
| 5,705,050 A | 1/1998 | Sampson et al. | 205/687 |
| 5,705,092 A | 1/1998 | Wellinghoff et al. | 252/187.21 |
| 5,707,739 A | 1/1998 | Wellinghoff et al. | 428/403 |
| 5,736,016 A | 4/1998 | Allen | 204/237 |
| 5,787,723 A | 8/1998 | Mueller et al. | 62/347 |
| 5,853,689 A | 12/1998 | Klatte | 423/478 |
| 5,878,583 A | 3/1999 | Schlosser et al. | 62/73 |
| 5,888,528 A | 3/1999 | Wellinghoff et al. | 424/405 |
| 5,901,564 A * | 5/1999 | Comeau, II | 62/264 |
| 5,914,120 A | 6/1999 | Wellinghoff et al. | 424/406 |
| 5,922,776 A | 7/1999 | Wellinghoff et al. | 514/772.3 |
| 5,965,264 A | 10/1999 | Barenberg et al. | 428/402 |
| 5,967,202 A | 10/1999 | Mullen et al. | 141/104 |
| 5,974,810 A | 11/1999 | Speronello | 62/66 |
| 5,980,826 A | 11/1999 | Barenberg et al. | 422/37 |
| 6,004,439 A | 12/1999 | Bakhir et al. | 204/260 |
| 6,046,243 A | 4/2000 | Wellinghoff et al. | 514/772.3 |
| 6,071,483 A | 6/2000 | Pastore | 422/255 |
| 6,071,539 A | 6/2000 | Robinson et al. | 424/466 |
| 6,077,495 A | 6/2000 | Speronello et al. | 423/477 |
| 6,171,558 B1 | 1/2001 | Simpson | 422/186.3 |
| 6,196,007 B1 | 3/2001 | Schlosser et al. | 62/73 |
| 6,238,643 B1 | 5/2001 | Thangaraj et al. | 423/477 |
| 6,363,734 B1 * | 4/2002 | Aoyagi | 62/264 |
| 6,607,696 B1 * | 8/2003 | Hamilton et al. | 422/37 |

FOREIGN PATENT DOCUMENTS

| | | | |
|---|---|---|---|
| DE | 2903436 A | * | 7/1980 |
| FR | 2757935 | * | 7/1998 |

* cited by examiner

DEVICE FOR HOLDING A CONTAINER FOR A COMPOSITION THAT PRODUCES AN ANTIMICROBIALLY ACTIVE GAS

FIELD OF THE INVENTION

The present invention relates to a device and method for cleaning and deodorizing a unit having an enclosed space not otherwise easily accessible for cleaning and deodorizing. The device and method of the present invention utilize the generation of an antimicrobial gas in an amount effective to reduce microbial populations including germs and fungi.

BACKGROUND OF THE INVENTION

Automatic ice making machines run essentially continuously using two basic systems. These systems are the coolant recycle refrigerant system and the water/ice system.

Problems exist which can impede the operation of an ice making machine, particularly those that run automatically for extended periods of time. One such problem that occurs is the formation and build-up of various biological growths including molds, yeast, fungi, slimes, other microbiological growths, and so forth. These microbiological growths, molds, yeast, fungi, and slimes form on the water-ice system surfaces, and can impede the flow of water through the system and can cause decreased heat transfer efficiency, particularly on the evaporator plates and ice forming molds on which ice is being made. Cleaning and sanitizing the machines typically requires a down-time. Automatic cleaning units for these machines that decrease the downtime and improve efficiency have now been developed. For instance, U.S. Pat. No. 5,289,691 describes an automatic self-cleaning, self-sterilizing ice making machine having a coolant/refrigerant system, a water-ice system, a cleaning/sterilizing system and a microprocessor operated control system interconnecting the above systems. This cleaning/sterilizing system has the capability of routinely cleaning and sterilizing surfaces in contact with circulating water/ice within the water/ice system in a way to provide clean surfaces and minimize maintenance costs and manpower involved in manually cleaning and scrubbing ice making surfaces or other water contacting surfaces which have become fouled by deposits.

However, while this automatic cleaning/sterilizing system is useful for the areas that come into contact with the water/ice, i.e. the ice bin, it does not reach those areas inside the upper portion or head portion of the ice machine above the condenser/ice making unit. Cleaning this area in a typical ice machine usually requires the removal of an access panel by means of multiple screws. Cleaning the corners of the head space manually can be difficult as parts of the ice making machine required for operation such as the water pump, are located in this area further compounding the difficulty of cleaning. Furthermore, the head space is a better incubating environment for microbial growths than the ice bin itself because the temperature is higher and the humidity is high. Gaseous chlorine dioxide in low concentrations (i.e. up to 1,000 p.m.) is known for its utility and effectiveness as an antimicrobial, i.e. fungicide and bactericide, and also as a deodorant. It is particularly useful where microbes and/or organic odorant are sought to be controlled on and around foodstuffs, as chlorine dioxide functions without the formation of undesirable side products such as chloramine or chlorinated organic compounds that can be produced when elemental chlorine is utilized for the same or similar purposes. For example, if a low concentration of chlorine dioxide gas can be maintained in contact with fresh produce for several days during shipping from the farm to the local retailer, the rate of spoilage of the produce can be decreased. Additionally, chlorine dioxide gas is also generally considered as safe for human contact at concentrations effective for deodorization and for most antimicrobial applications because the required concentrations are so low.

U.S. Pat. No. 6,077,495 describes a method, composition, and system for generating chlorine dioxide gas in a controlled release manner.

U.S. Pat. No. 5,974,810 describes a method and composition for producing ice having substantially no undesirable taste and odor characteristics comprising freezing ice in the presence of chlorine dioxide gas.

SUMMARY OF THE INVENTION

The present invention describes a method and device for reducing the population of microbes in units which have enclosed spaces not easily accessible for cleaning/deodorizing in a convenient and efficient manner. An example of such a unit is the head portion of an ice machine.

More particularly, the unit of the present invention has an interior and an exterior. The unit also has an access port which may be opened from the exterior of the unit to permit placement and replacement of a container which is permeable to liquid water or water in vapor form and which contains a composition for generating an antimicrobial active gas upon exposure to water or water in vapor form. The unit has a device for holding the container which is accessible through the access port which retains the container within the interior of the unit at a location which is exposed to ambient air within the interior of the unit.

In some embodiments of the present invention, the unit has a top and a front and the holder is in the front or top of the unit. The unit may also have sides and/or a back or bottom in which the holder may be placed. Suitably, the holder is in a convenient location which is easily accessible.

In one particular embodiment, the container is in the form of a sachet, bag or packet, and the composition generates chlorine dioxide gas upon exposure to water in vapor form or moisture.

The unit may also include an indicator device activated upon each placement or replacement of the container, which provides a signal on the exterior of the unit when the container needs replacement.

The present invention is particularly useful in enclosed units wherein it is difficult to access the interior for cleaning and sanitizing. For instance, the device is useful in refrigeration units, storage lockers of any type wherein access is not easily gained, and so forth.

DETAILED DESCRIPTIONS OF THE PREFERRED EMBODIMENTS

Figure 1:
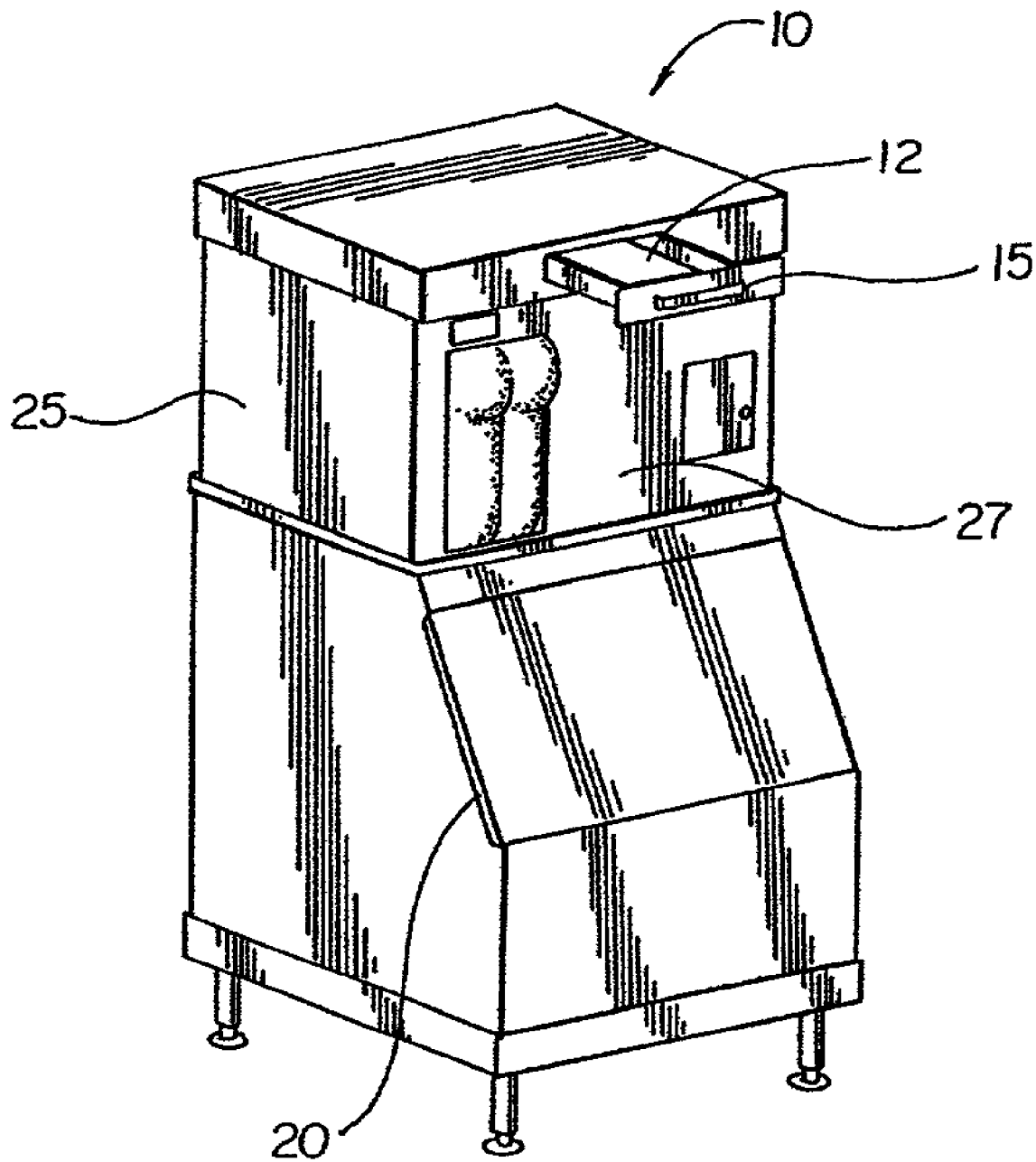
FIG. 1 is a perspective view of an ice machine showing one embodiment of the present invention.

FIG. 1 illustrates one particular embodiment of the present invention and illustrates an ice producing machine generally at 10. The head portion 25 of ice machine 10 houses an access port 12 which provides access to the interior (not shown) of the ice machine. Ice machine 10 also has a holder 15 for holding a container which has a composition that generates an antimicrobial active gas upon exposure to water or water in vapor form. The holder 15 in this embodiment is in the form of a drawer which slides easily through the access port 12 and into the interior (not shown) of the head portion 25 of the ice machine 10. FIG. 1 also shows the front access panel 27 which would require removal on a much more regular basis for sanitizing/deodorizing of the interior (not shown) of the head portion 25 without the access port 12 and holder 15 of the present invention.

In the embodiment shown in FIG. 1, the access port/holder is in the form of a slot/drawer. However, any access port and holder may be utilized in the present invention to provide easy access to the interior of an enclosed space. For instance, removable trays, pivoting pockets, slots, pocket doors, swinging doors, and so forth may be utilized. The access port/holder must allow air to flow around the container and must not be enclosed so that the gas may escape into the interior of the enclosure.

The access port/holder may suitably be provided on the front, top or side panels of the enclosed unit.

Figure 2:
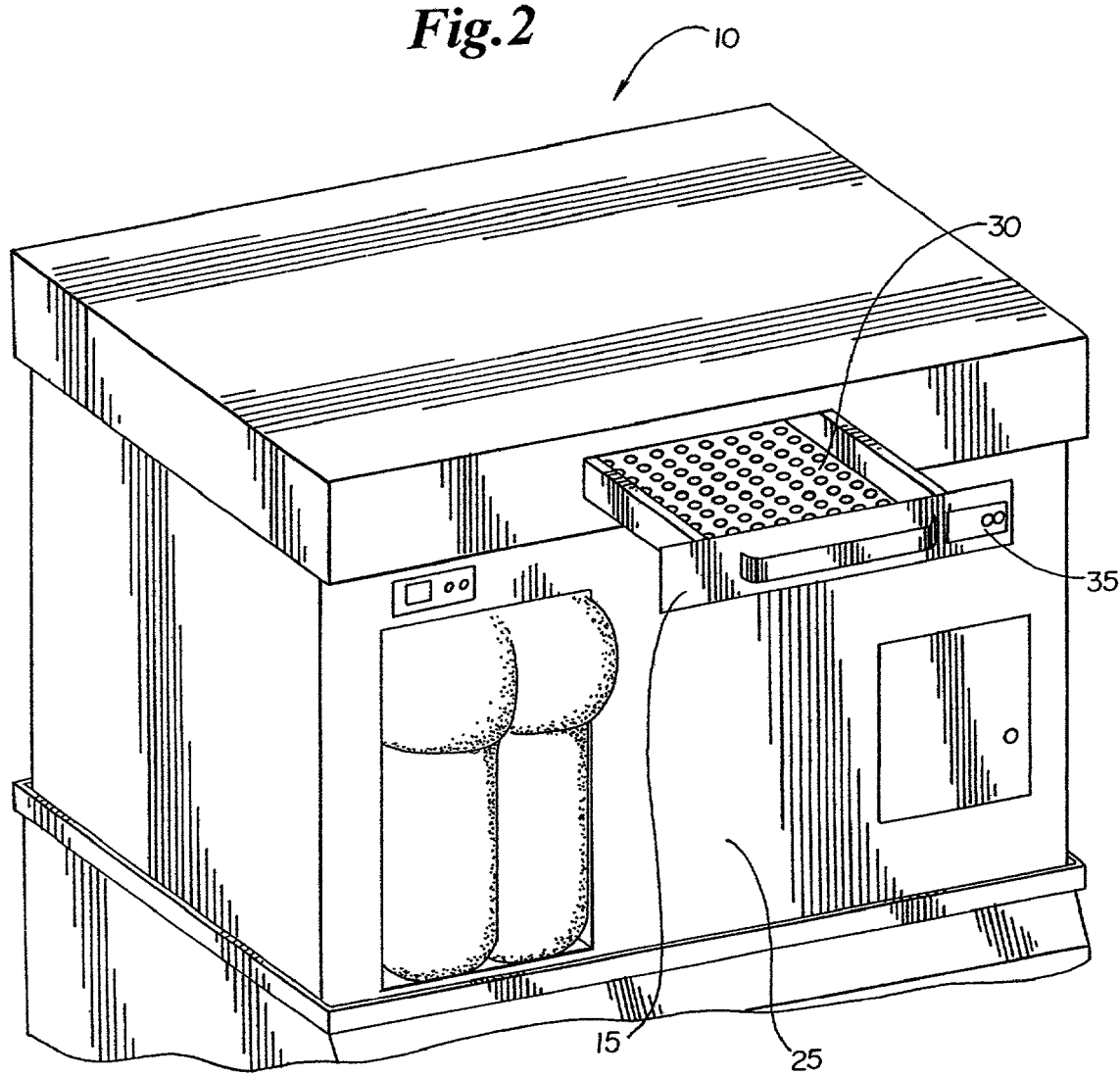
FIG. 2 is a different view of the same ice machine as shown in FIG. 1.

FIG. 2 shows an expanded view of the same ice machine 10 as shown in FIG. 1. The holder 15 in this embodiment also shows an indicator device 35 which is activated upon placement or replacement of the container holding the composition that generates the antimicrobial active gas upon exposure to water or water in vapor form. This indicator device 35 may be in the form of a red/green LED, for instance.

Figure 3:
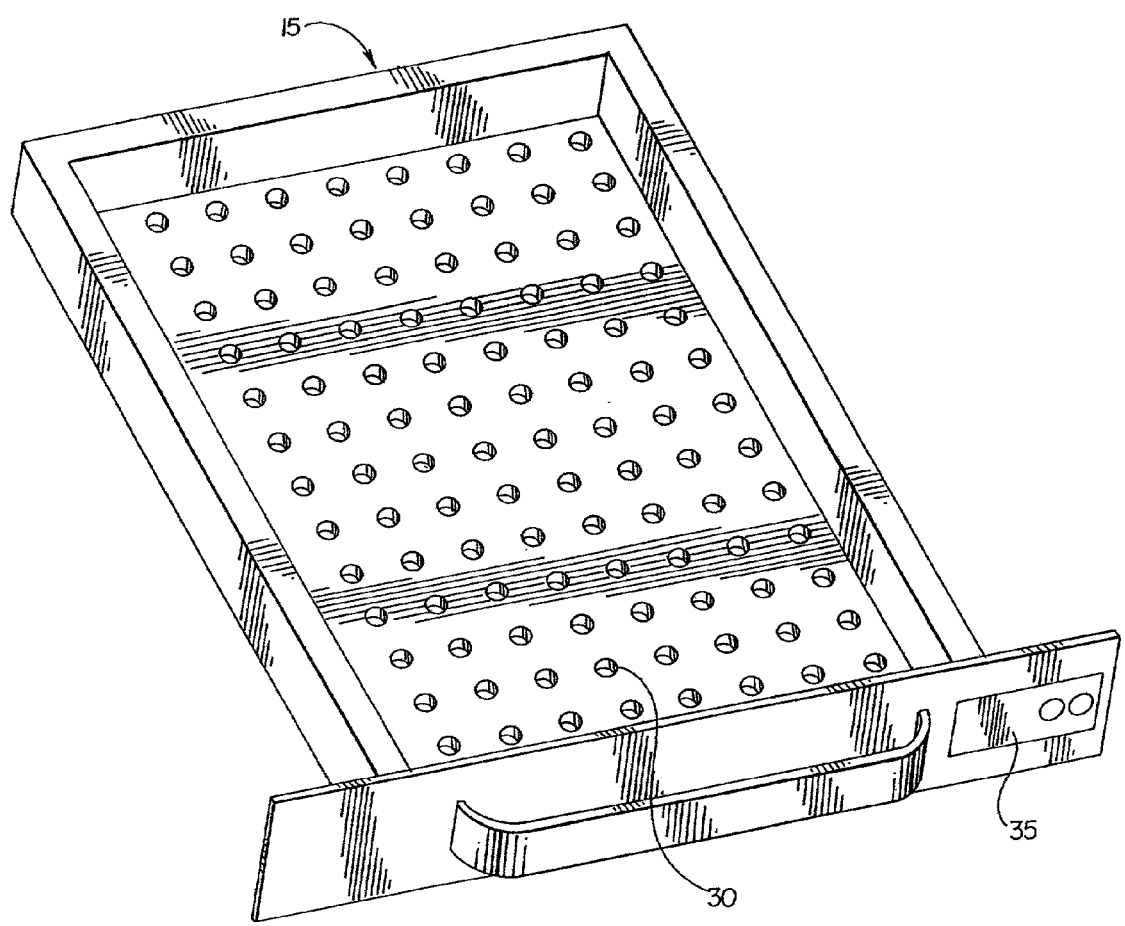
FIG. 3 is a perspective view of an embodiment of the device of the present invention.

FIG. 3 shows a more expanded view of the holder 15 designed for holding a container having the gas generating composition of the present invention. As can be seen from the figure, the holder 15 further has perforations 30 which allow escape of the gas into the interior (not shown) of the head portion 25 of the ice machine 10.

Figure 4:
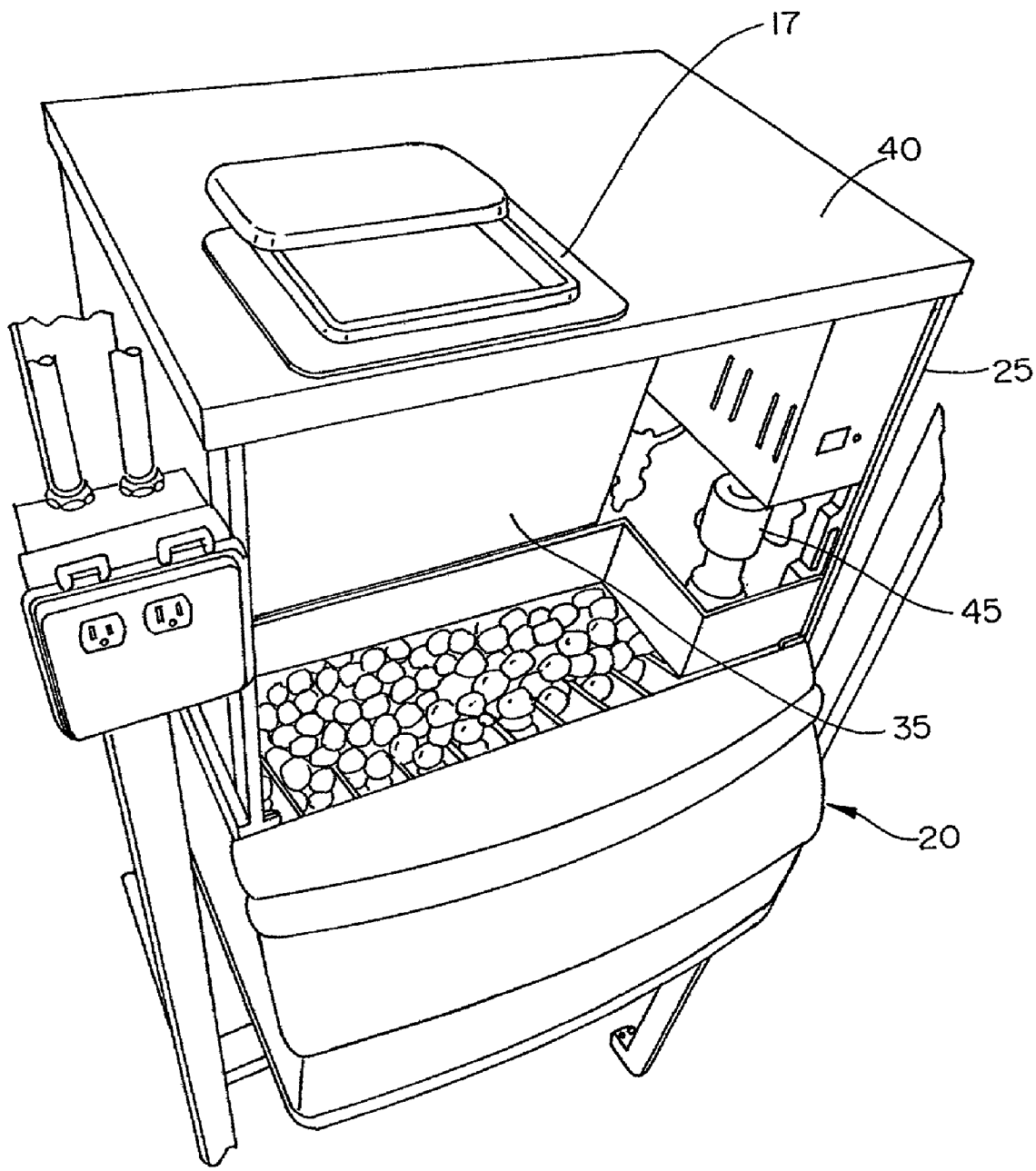
FIG. 4 is a perspective view of an alternative form of the embodiment of the present invention.

FIG. 4 shows an alternative embodiment of the present invention in which the holder 17 for holding the container having the gas generating composition of the present invention is located on the top surface 40 of the head portion 25 of the ice machine 10. The holder 17 in this instance sits inside of the access port (not shown) which cannot be seen. In this figure, the access panel 27 has been removed making the interior 35 of the head portion 25 of the ice machine 10 clearly visible. As can be seen, the interior 35 of the head portion 25 houses a water pump 45 among other things.

Ice machines of the type described above are found in U.S. Pat. No. 5,289,691, U.S. Pat. No. 5,408,834, U.S. Pat. No. 5,586,439, U.S. Pat. No. 5,787,723, U.S. Pat. No. 5,878,583, U.S. Pat. No. 6,196,007 B, and so forth, each of which is incorporated by reference herein in its entirety. These ice machines are intended for exemplary purposes only. One of skill in the art would understand that various modifications could be made to the ice machines described herein, and that other completely different configurations could be utilized without departing from the scope of the present invention.

The device of the present invention is designed so as to allow easy access to the interior of an otherwise enclosed space not easily accessible for cleaning and deodorizing. Such device may be utilized in any enclosed area or machine where mold, mildew, fungi, yeast, or other bacteria may be problematic.

The device may also include an indicating device or change out indicator such as a timing device which signals the need to replace the container. The indicator may provide some sort of signal in response to a predetermined time interval between openings of the access port, for instance. The device may be activated upon each placement or replacement of the container, and provides an indicator signal on the exterior of the unit when the container needs replacement. This may be in response to a predetermined time interval between openings of the access port.

The signal may be an alarm or a green/red LED that is activated after a given time interval. The change out indicator may be provided on the front of the unit, or may be held by a secondary holder inside the first holder. As shown in FIGS. 1–3, above, the indicator may be provided as a display on the front of the holder which in the embodiments shown in FIGS. 1–3, is in the form of a drawer.

Another method of indicating the need to change the container is to use a sticker whereby the dates for the required change are indicated.

Or, for certain gaseous substances, a detector or sensor may be utilized to monitor the amount of gas in the head space inside the interior of the ice machine and when the concentration becomes too low, an alarm will sound or an LED may indicate the low concentration with a red/green color change.

Any composition capable of producing an antimicrobially active gas may be utilized in the device and method of the present invention. Most conveniently, this is accomplished by exposing the composition to liquid water or water in vapor form. Such generation of gas is desirably accomplished in a controlled release manner in amounts effective to reduce microbial populations including mold, yeast, fungi, and other microbes. In some instances, the gas may also act as a deodorant thereby reducing offensive and noxious fumes.

Examples of gases that may suitably be generated in aqueous solution in this fashion include, but are not limited to, chlorine dioxide, halogens including chlorine, bromine and iodine, ozone, ethylene oxide, or other vapor emitting corrosion inhibitors.

Typically, generation of a gas in this manner will involve at least two reactants. For instance, in some embodiments of the present invention, chlorine dioxide is generated by using a mixture of at least one metal chlorite and at least one second material which is capable of reacting with the metal chlorite to produce chlorine dioxide gas in the presence of water or water vapor, but not in the substantial absence of liquid water or water vapor, typically, an acidic component. At the time of use, the mixture is exposed to atmospheric water vapor resulting in the production of chlorine dioxide gas at a sustained concentration of about 0.025 to about 1000 ppm. The generation of chlorine dioxide using such methods are described, for example, in U.S. Pat. No. 4,547,381, U.S. Pat. No. 4,585,482, U.S. Pat. No. 5,974,810, U.S. Pat. No. 6,077,495, U.S. Pat. No. 5,650,446, U.S. Pat. No. 5,695,814, U.S. Pat. No. 5,707,739, U.S. Pat. No. 5,091,107, U.S. Pat. No. 5,888,528, U.S. Pat. No. 5,922,776, U.S. Pat. No. 5,965,264, U.S. Pat. No. 5,980,826, U.S. Pat. No. 6,046,243, and so forth, all of which are incorporated by reference herein in their entirety.

The mixture of metal chlorite, an acidic material, and any other desired additives may be packaged for shipment and storage in containers made of materials which are resistant to the passage of liquid water and water vapor. Examples of such materials include metal cans, glass jars, foil pouches, and barrier layer polymer laminates.

Chlorine dioxide acts as a deodorant by reducing noxious compounds including, for example, aldehydes, amines and thiols which are oxidized respectively to alcohols or acids, nitro compounds or various intermediates such as nitroso compounds, and to disulfide or oxides of sulfur.

The mixture of the metal chlorite and the acidic material may be used as a powder, used as formed shapes, or packaged and retained for use in any material which is gas permeable.

Suitably, the packaging material retained for use is substantially impervious to liquid water, but is permeable to water in vapor form. One particular class of materials suitable for use herein include micro porous nonwoven hydrophobic polymer sheet materials such as TYVEK® nonwoven polyethylene available from DuPont and GORE-TEX® woven polytetrafluoroethylene available from W. L. Gore & Associates both of which are commercially available. Such materials are typically flexible in nature and are quite suitable for making packages in the form of a sachet, bag or packet.

These materials allow water vapor to enter into the package and react with the mixture and also enable the resulting gas, for instance, chlorine dioxide gas, to be released from the package and enter the atmosphere. Particles larger than about 0.3 microns, for instance, are filtered or blocked, and not allowed to pass through the fabric. Such materials are substantially impervious to water in liquid form. Such materials may require packaging, storage and shipment in a container that would not allow the passage of moisture in any form in order to prevent a premature reaction. Shrink wrap is one form of packaging that may be utilized in the present invention. If a sachet, bag, pouch, or similar form is used, these could be available in 6-, 12-and 24-pack cases.

Materials that do not allow water to pass in any form may also be utilized in a packaging form that would require opening prior to use. Such a package may be more difficult to utilize because the transfer of water vapor into the package would not be as evenly distributed as in the case of a material permeable to water in vapor form.

In one embodiment, the reactants are acidified calcined metakaolin clay and sodium chlorite, both of which are in solid form. The reactants are packaged in a sachet formed from either TYVEK® or GORETEX® materials. The amount of reactants utilized may be between 50 and 100 g with sodium chlorite being about 5 wt-% of the composition and the acidified clay being about 95 wt-% of the composition. Chlorine dioxide delivery using this embodiment is about 1–2 ppm in the first several hours, about 0.5 to 1.0 ppm (t½) after about 24 hours, and levels off to about 0.1 ppm for about 30 days. The sachets would require changing about every 30 days.

Alternatively, a self-contained composition for the generation of gas may be utilized in the present invention wherein a shrink-wrapped container is equipped with a battery such as a 9-volt battery, and a circuit. A charge causes the wire to heat and melt the shrink wrap thereby exposing the chemicals to the moisture in the ambient air. The battery may be further equipped with a timing device.

The rate at which chlorine dioxide is generated will, to a certain extent, depend on the relative humidity of the environment in which the reactants are placed. For instance, the method of the present invention can be conducted under low humidity conditions (e.g. 10% relative humidity) up to 100% high humidity conditions. As previously indicated, the amount of chlorine dioxide gas generated per given amount of the mixture will depend, in part, on the relative humidity of the surrounding atmosphere. In general, higher humidity will result in a higher concentration of chlorine dioxide gas.

The success of the method of the present invention for treating ice machines depends on the level of chlorine dioxide that is present in the head space of the ice machine, i.e. the space above and around the reactants.

The amount of chlorine dioxide in the head space is also dependent on the temperature of the water. When the water temperature is less than about 50° F., considerably less chlorine dioxide is observed in the head space. This of course is a result of the very low vapor pressure of chlorine dioxide.

The materials of this invention may also be used to help prevent the incorporation of unwanted substances (including possibly toxic substances) which may affect the taste and odor in ice produced by ice machines, particularly in large volume ice production such as in commercial applications. It is well known that after prolonged use, the ice producing chambers of such ice machines can accumulate microbes (including pathogenic microbes) and microbial films which may emit harmful or unpleasant smelling and tasting gaseous byproducts and other byproducts. Such byproducts can accumulate in or on the ice being produced either before, during or after the water freezing process. However, it is believed that the taste and odor of the ice being produced will be less affected and will not deteriorate to a substantial degree when materials of the present invention are used to generate and maintain a concentration of chlorine dioxide gas from between about 0.01 to about 10.0 ppm, and preferably from about 0.01 to about 1.0 ppm within the ice producing chamber of an ice machine. It is believed that the chlorine dioxide gas produced in accordance with the practice of this invention destroys the unpleasant smelling and tasting microbial byproducts so that they do not contaminate the ice. At higher concentrations of chlorine dioxide gas, the microbes themselves may be destroyed by the chlorine dioxide gas.

Optionally, other items may be utilized with the present invention. For instance, a desiccant pad may be utilized for moisture removal, sodium bicarbonate may be used for odor removal, a monitoring device may be used for monitoring temperature and humidity, a change out indicator, may be used for indicating when the composition needs to be changed, and so forth. Such items may be easily placed within the interior of enclosed units that are not easily accessible from the exterior of the unit using the present invention. These items could be provided in a secondary holder within the first holder, for instance, or they may be provided in their own access port/holder combination.

While the particular embodiments above illustrate the use of the inventive concept in a refrigeration unit, i.e. ice machine, it is important to note that the present invention may be utilized in any enclosed space not easily accessible for sanitizing/deodorizing. For example, other refrigeration units such as soda machines, produce storage lockers, cleaning equipment/supply lockers, lockers in gyms, garbage receptacles, closets, and so forth. Other types of applications include in seasonal vacation homes which are often closed up for certain periods of time, bathroom stalls, for bar use, and so forth.

One of ordinary skill in the art would understand that the embodiments described above are by way of exemplification. The inventive concepts may be modified without deviating from the scope of the present invention.

The following non-limiting examples further illustrate the present invention.

EXAMPLES

In the following examples, each sachet contained 95% acidic metakaolin calcined clay available from various sources and 5% sodium chlorite. The sachets were manufactured of SENTREX® breathable, water-proof material available from Kimberly-Clark in Neenah, Wis.

Example 1

Two 50 g sachets were mounted in the condenser area of a model # Q400 ice machine manufactured by Manitowoc Co. in Manitowoc, Wis. The condenser area measured 3.25 cu feet. The ice machine produces 400 lbs of ice per day. Dragger tubes were utilized to measure the chlorine dioxide level in the top of the ice machine and in the door two weeks after installation of the sachets. The concentration of chlorine dioxide was found to be 0.14 p.m. in the top of the machine, and 0.09 p.m. in the door of the ice machine.

Example 2

Four 50 g sachets were installed in a Manitowoc Ice Machine Model A400. The chlorine dioxide concentration was measured in the top of the ice machine and in the door 24 hours after installation and 168 hours after installation. The following results were achieved.

TABLE 1

|  | Top | Door |
| --- | --- | --- |
| 24 hours | 0.70 p.m. | 0.19 p.m. |
| 168 hours | 0.10 p.m. | — |

The amount of chlorine remaining in the sachets was measured using titration methods and calculated as a percentage of residual chlorite and found to be 64%, 57%, 83% and 62% remaining.

The invention claimed is:

1. A unit comprising an enclosed space not easily accessible for cleaning and deodorizing, the unit having an interior and an exterior, the unit comprising:

a container permeable to water or water vapor, holding a composition which generates an antimicrobially active gas;

an access port in the unit openable from the exterior of the unit to permit placement and replacement of the container;

a holder for said container, accessible through the access port, which retains the container within the interior of the unit at a location exposed to the ambient air within the interior; and an indicator device providing an indicator signal in response to a predetermined time interval between openings of said access port.

2. The unit of claim 1 wherein said composition comprises sodium chlorite and an acidic component.

3. The unit of claim 1 wherein said composition generates chlorine dioxide gas.

4. The unit of claim 1 wherein said holder is a drawer, pivoting pocket, slot or tray.

5. A unit as in claim 1 wherein said indicator signal is a light or an alarm activated upon passage of said time interval.

6. The unit of claim 1, said unit having a top and a front wherein said holder is in the top or front of said unit.

7. The unit of claim 1 wherein said container holds from about 50 g to about 500 g of said composition.

8. The unit of claim 1 wherein said composition is a solid, a liquid or a combination thereof.

9. A unit as in claim 1 wherein said container is comprised of a microporous nonwoven hydrophobic polymer sheet material.

10. The unit of claim 9 wherein said container is comprised of a nonwoven polyethylene or a nonwoven polytetrafluoroethylene.

11. The unit of claim 1 wherein said container is a sachet, bag or pouch.

12. A unit as in claim 1 wherein said access port is configured such that the contents within the interior of the unit, other than said container, may not be accessed therethrough.

* * * * *